United States Patent [19]

Krabetz et al.

[11] 4,297,247

[45] Oct. 27, 1981

[54] PREPARATION OF COATED CATALYSTS

[75] Inventors: Richard Krabetz, Kirchheim; Walter Herrmann, Mannheim; Heinz Engelbach, Limburgerhof; Peter Palm, Gerolsheim; Karl Sommer, Ludwigshafen; Heinrich Spahn, Mannheim, all of Fed. Rep. of Germany

[73] Assignee: BASF Aktiengesellschaft, Ludwigshafen, Fed. Rep. of Germany

[21] Appl. No.: 126,385

[22] Filed: Mar. 3, 1980

[30] Foreign Application Priority Data

Mar. 12, 1979 [DE] Fed. Rep. of Germany ....... 2909671

[51] Int. Cl.³ .................... B01J 23/22; B01J 23/28; B01J 23/30; B01J 23/72
[52] U.S. Cl. .................... 252/468; 252/461; 252/467; 252/469; 252/470; 252/477 R; 427/215; 562/534; 562/535
[58] Field of Search ............... 252/461, 467, 468, 469, 252/470; 427/215

[56] References Cited

U.S. PATENT DOCUMENTS 3,956,377 5/1976 Dolhyj et al. .................. 252/462 X
4,077,912 3/1978 Dolhyj et al. ...................... 252/461

FOREIGN PATENT DOCUMENTS 10218 8/1976 Australia .
640455 7/1950 United Kingdom .

Primary Examiner—W. J. Shine
Attorney, Agent, or Firm—Keil & Witherspoon

[57] ABSTRACT

A coated catalyst comprising (a) an inert carrier having a particle diameter of not less than 100 μm and a surface area of up to 20 m²/g and (b) a coating which firmly adheres to the outer surface and in the edge zone, near the surface, of the carrier particles, and which contains the catalytic material, can be prepared by applying the catalytic material in the form of a powder of particle size not more than 300 μm, in the presence of water, to the vigorously agitated carrier by a process wherein catalytically active material in an amount of from 1 to 40 g/minute/liter of carrier, and water in a weight ratio of catalytic material to water of from 1:1 to 30:1, are applied continuously and spatially separate from one another, each at a constant speed, onto the carrier particles, which may or may not have been pre-moistened with water in an amount of up to 95% of the particle absorbency, in such a way that the water content of the coating which forms is less than the maximum degree of saturation of the coating of catalytic material.

6 Claims, No Drawings

PREPARATION OF COATED CATALYSTS

The present invention relates to a novel process for the preparation of coated catalysts by applying a pulverulent catalytic material, in the presence of water, to agitated carrier particles.

British Pat. No. 1,346,943 discloses that coated catalysts comprising a carrier and a coating, applied thereto, of a catalytic material can be prepared by applying the catalytic material to the carrier by plasma spreading or flame spraying. A precondition for the applicability of the process is that one or more of the principal components should be fusible at the operating temperature of the flame-spraying gun or of the plasma torch. The catalysts, obtained by conventional atomizing application in a Comparative Example, and possessing coatings containing $V_2O_5$, $MoO_3$ and/or $WO_3$, admittedly give a yield of only 13.8% in the oxidation of indans, whilst the process of British Pat. No. 1,346,943 gives a yield of 45%, but nevertheless the activity of active materials produced form the melt is very unsatisfactory for many processes, and the production of free-flowing material, which the process requires, is difficult and expensive.

U.S. Pat. No. 3,956,377 discloses a special process for the preparation of coated catalysts for the gas phase oxidation of acrolein or methacrolein to acrylic acid or methacrylic acid, wherein, for example, molybdenum oxide, vanadium oxide and metallic tungsten powder are treated in water by refluxing and the resulting slurry is evaporated and the residue dried for several days at 115° C. The active catalyst material thus obtained is then applied to the carrier, which has previously been moistened with water, by tumbling the moist carrier in a powder of the active catalyst. Such a process is also disclosed in U.S. Pat. No. 4,077,912. Catalysts prepared in this way are frequently relatively inactive, in particular since the porosity of the carrier, and hence its water absorbency, limit the proportion of catalytic material in the coating. A further disadvantage of the method is that the degree of moistening of the particular surface layer during the coating process does not assume a stable value, and this detracts from the adhesion and leads to agglomeration of the particles, with formation of twins and triplets, and to varying thicknesses of coating.

Finally, U.S. Pat. No. 2,035,606 (page 3), British Pat. No. 1,385,496 and German Laid-Open Application DOS No. 2,626,887 disclose that coated catalysts can be prepared by spraying aqueous suspensions of the catalytic material onto the agitated carrier particles, which can, for example according to U.S. Pat. No. 3,562,185 and British Pat. No. 1,385,496, be heated to above 150° C. or, when synthetic resin dispersions are additionally used, to about 70°–130° C. However, given the abrupt evaporation of the suspending medium if the carrier particles are at, for example, 150° C. or above, the coated catalysts obtained in general exhibit insufficient abrasion resistance of the catalytic coating and a large loss of active material during coating. If synthetic resin dispersions are used additionally, the coating process is made difficult by film-forming processes which are difficult to control and furthermore the synthetic resin must subsequently be burned away, which can result in a loosening of the structural lattice and to thermal impairment of the activity. In the process of German Laid-Open Application DOS No. 2,626,887, which can be carried out at 25°–80° C., agglomeration of the sprayed particles can occur and the adhesion of the coating is frequently unsatisfactory.

We have found that a coated catalyst comprising (a) an inert carrier having a particle diameter of not less than 100 μm and a surface area of up to 20 m²/g and (b) a coating which adheres firmly to the outer surface and in the edge zone, near the surface, of the carrier particles and which contains the catalytic material, can be prepared advantageously by applying the catalytic material, in the form of a powder having a particle size of not more than 300 μm, in the presence of water, to the vigorously agitated carrier if catalytically active material in an amount of from 1 to 40 g/minute/liter of carrier, and water in a weight ratio of catalytic material to water of from 1:1 to 30:1, are applied continuously and spatially separate from one another, each at a constant speed, onto the carrier particles, which may or may not have been pre-moistened with water in an amount of up to 95% of the particle absorbency, in such a way that the water content of the coating which formes is less than the maximum degree of saturation of the coating of catalytic material.

If porous carriers are employed in the novel process, their mean pore diameter should preferably be greater than 20 μm, and the particle size of the catalytic material should in that case be less than the mean particle diameter of the carrier.

We have found, surprisingly, that the process according to the invention, in contrast to conventional processes, gives, even when used to prepare catalyst batches on an industrial scale, coated catalysts having a very uniform distribution of the active material on the carrier particles, without agglomeration of the catalyst particles, and with a uniform bulk density and high abrasion resistance; this permits particularly uniform and rapid filling of tube-bundle reactors and contributes to improving the average selectivity and space-time yield of industrial batches. A further surprising advantage of the process according to the invention is that even if the proportion by weight of the active material is more than 100 and even as much as 150% by weight, based on the carrier, or the coating thickness is greater than 0.8 mm, for example 1.5 mm, the coated catalysts obtained still have good abrasion resistance, which is important for the industrial use of coated catalysts, for example for the oxidation of isobutene to methacrolein.

The conventional carriers, such as aluminum oxides, for example α-$Al_2O_3$, silicon dioxide, thorium dioxide, zirconium dioxide and silicates, eg. magnesium silicate and aluminum silicate, as well as silicon carbide, may be used for the novel process of preparation of coated catalysts. The carrier material particles may or may not be molded, but molded carriers, for example balls or rings, having a pronounced surface roughness are preferred. The diameter of the carrier particles should be not less than 100 μm and is preferably from 0.5 to 12 mm, especially from 1 to 9 mm. The carriers may be porous or non-porous, but porous carriers should have a mean pore diameter of not less than 20 μm and preferably not less than 50 μm. If porous carriers are used, the particle size of the active material should in general be less than the mean pore diameter of the carrier. If the finished catalysts are to be employed for reactions carried out at above about 350° C., it is preferred to use carriers whose inner surface area is less than 5 m²/g, in particular less than 2 m²/g, and whose porosity is in general from 0 to 10% and preferably less than 5%. If the finished coated catalysts are to be employed at below about 300° C., carriers with porosities of greater than 5% or greater than 10% may also be advantageous. Carriers which have a porosity of less than 30% and in particular less than 5% are preferred for the preparation of the novel coated catalysts.

The novel process is not restricted to specific types or compositions of the catalytic material; in principle, virtually any catalytic material can be applied to carriers by the novel process. All known conventional catalyst materials, especially those suitable for highly exothermic reactions, may be used, especially those based on metal oxides, metal oxide mixtures and/or mixed metal oxides, such as are employed, in particular, for catalytic oxidation reactions, for example the catalytic oxidation of α-olefins, eg. propene and isobutylene, to α,β-olefinically unsaturated aldehydes, especially acrolein and methacrolein, and the catalytic oxidation of hydrocarbons, eg. of butane or butene to maleic anhydride, of o-xylene to phthalic anhydride and of o- and p-substituted alkylbenzenes to o- and p-substituted benzaldehydes, as well as the oxidative dehydrogenation of hydrocarbons or alcohols and the oxidation of aldehydes. Such catalytic materials are described, for example, in British Pat. Nos. 1,491,750 1,249,290 1,351,218 1,416,099 and 1,305,810. Catalytic materials of particular interest are those usually employed for the oxidation of acrolein or methacrolein to acrylic acid or methacrylic acid and based on oxides or mixed oxides which contain molybdenum, vanadium, tungsten, copper and/or manganese and/or iron and may or may not contain minor amounts of alkali metals and alkaline earth metals as well as other metal oxide components; such materials are in particular described in German Laid-Open Application DOS No. 2,626,887. Catalysts which have proved particularly suitable for the gas phase oxidation of acrolein with oxygen-containing gases to give acrylic acid, under conventional conditions of pressure and temperature, are coated catalysts which have been produced by the novel process and wherein the catalytic material has the composition

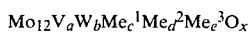
$$Mo_{12}V_aW_bMe_c^1Me_d^2Me_e^3O_x$$

where

Me¹ is Cu and/or Fe, with or without Mn,

Me² is one or more metals from the group consisting of Sb, Sn, Cr, Nb, Ta and Ni, and Me³ is an alkali metal and/or alkaline earth matal, a is from 0.5 to 15, preferably from 2 to 6, b is from 0.1 to 6, preferably from 0.5 to 3, c is from 0.1 to 6, preferably from 1 to 3, d is from 0 to 6, preferably from 0 to 1, and e is from 0 to 0.1, especially from 0.001 to 0.1, and x is the number of atoms required to saturate the valencies of the other components.

Active materials based on mixed oxides containing molybdenum, vanadium, phosphorus and an alkali metal or $NH_4$ are particularly suitable for the oxidation of methacrolein.

In the novel process, the catalytic material is as a rule applied in its finished catalytically active form, for example as a calcined mixed oxide which after calcination has been milled to the envisaged particle size. In some cases it is, however, also advantageous only to calcine the catalytic material after the coated catalyst has been prepared. The particle size of the active catalytic material is less than 300 μm, in most cases less than 150 μm, preferably to the extent of 90% by weight less than 50 μm, and especially from 1 to 45 μm. If the catalysts are to contain metals as the active catalytic material, the metals may be applied as oxides, in which case the coated catalysts obtained are reduced after drying; the reduction can be carried out immediately prior to their use in an industrial reactor. However, even in this case it is preferred to coat the carrier with the active catalytic material, ie., in the present instance, with the catalytic metals (which may be precipitated on oxidic components), so that an after-treatment is not needed.

The amount of active catalytic material on the finished coated catalyst is in general from 3 to 300, especially from 5 to 200, % by weight based on the weight of the carrier.

In practice, the process can be carried out in rotatable vessels, for example inclined rotating dishes which preferably have an angle of inclination of from 30° to 60°, or, advantageously, in coating kettles. The vessel is preferably filled to the extent of from 20 to 80% of its volume with the carrier particles, and its speed of revolution is in general from 1 to 60 per minute, depending on the diameter, thereby producing vigorous agitation of the carrier particles. The water can be sprayed onto the agitated carrier particles through, for example, one-material or two-material nozzles. In the latter case, the water which may evaporate into the propellant gas must be taken into account in deciding the amount of water to be sprayed onto the carrier.

The dry catalytic material can be applied to the carrier particles by, for example, a metering screw or belt weigher with conveyor chute, with or without a distributing device. The amount of dry catalytic material delivered is from 1 to 40 g, preferably from 1 to 25 g, per liter of carrier particles per minute, and the weight ratio of dry catalytic material to water is from 1:1 to 30:1 and preferably from 2:1 to 10:1; the rate at which the two components are metered in is kept virtually constant and is selected so that the water content of the coating which forms is less than the maximum degree of saturation of the coating of catalytic material, and is in general from 40 to 97, especially from 40 to 92, preferably from 60 to 87, % of this maximum degree of saturation. The maximum degree of saturation of the coating corresponds to the moisture content at which the catalytic particles start to agglomerate and no longer roll through the apparatus as isolated particles. As an approximation, the maximum degree of saturation of the coating of catalytic material is the amount of water in g which is taken up by 100 g of the catalytic material, in the form in which it is employed in the preparation of the coated catalysts according to the invention, at room temperature (22° C.), if the powder is stirred in a porcelain dish and the water is added dropwise over from 5 to 10 minutes until all the powder has agglomerated and the surface of the agglomerates begins to become moist and tacky.

Accordingly, the progressively coated carrier particles should, during coating, be sufficiently moist in their edge layer to take up the continuously delivered powder completely and bind it firmly, but should not be so moist that the carrier particles agglomerate in the water-spraying zone and no longer roll as isolated particles.

In the process according to the invention the carrier particles should in most cases be pre-moistened with not less than 0.1%, of their weight, of water before adding the catalyst powder. The requisite premoistening depends on the water absorption of the carrier particles and increases with their porosity. Non-porous carrier particles do not have to be pre-moistened.

In the case of carrier particles having a low porosity, of up to 5%, such as are preferred for the novel process, good results have been obtained by premoistening with from 0.1 to 2%, preferably from 0.5 to 1.5%, of the weight of the carrier particles, but this pre-moistening should at most amount to 95% of the water absorbency. With porosities greater than 5%, premoistening with from 5 to 30, preferably from 10 to 25, % of the water absorbency is in general advantageous. Carriers particles having a porosity of up to 5%, ie. very non-porous carriers, should have a very rough surface and give coated catalysts which, for a comparable activity, are in general more selective than similar coated catalysts which have been prepared from substantially more porous carrier particles.

The water absorbency is the amount of water in g which is taken up by 100 g of the carrier employed, if the latter is saturated by boiling with water and cooled by immersion in cold water at room temperature, after which the superficially adhering water is allowed to drain off into a slightly moistened filter paper.

The relative position of the catalyst powder feed and water feed, which should be spatially separate, is also a factor in the formation of a firmly adhering coating of uniform thickness. In particular, the catalyst powder should in general be introduced outside the spray cone of the water (which is preferably sprayed in through a nozzle), in order to prevent premature agglomeration of the catalyst powder particles. The partially coated carrier particles, which, in the water spray zone, are kept at an incomplete degree of moistening, which is constant with time, in the surface edge layer, taken up the fed-in catalyst powder at a constant speed and this powder becomes compressed on the outer particle surface, to form a coherent coating, as a result of the motion, for example the rolling motion, of the catalyst particles. Particularly with a high catalyst powder: water ratio, and slow addition of catalyst powder and water, a hard abrasion-resistant coating is obtained even during the coating process. In general, however, it is advantageous if, after completion of the coating process, the coated carrier is dried at from 60° to 150° C., especially from 70° to 120° C. The drying can advantageously be carried out in the coating apparatus by indirect heating or, preferably, by introduction of air, for example at from 20° to 300° C., especially from 20° to 150° C., with slow agitation of the material, until either the latter has reached a temperature of about 100° C. or a certain residual moisture of the coated catalyst particles is reached. The residual moisture should in general be less than 2%, preferably from 0.1 to 1.5%, by weight, based on the coated catalyst.

The coated catalysts can, if required, be converted to the active state by an after-treatment, for example calcination or reduction, for instance if the constituents of the catalytic material have been applied in an inactive form to the carrier. In the preferred embodiment, an after-treatment is not needed since the active material is applied in the catalytically active calcined state to the carrier particles.

A particular advantage of the novel process is that coated catalysts with coatings built up in layers from two or more different active materials can be produced in a single procedure.

In the Examples which follow, percentages are by weight.

EXAMPLE 1

(a) Preparation of the catalyst

A catalytic material having the composition $Mo_{12}V_3W_{1.2}Cu_{2.2}O_{49.3}$ is prepared as follows:

A solution of 26 kg of copper(II) acetate in 350 kg of water, as well as 10 kg of copper hydroxide carbonate, are added to a solution of 32.3 kg of ammonium paratungstate, 35 kg of ammonium metavanadate and 212 kg of ammonium heptamolybdate in 1,400 kg of water at 95° C., and the mixture is spray-dried at 110° C. The product is then kneaded with 0.15 kg of water per kg of solid, dried at 140° C. and subjected to a first calcination for 2½ hours at a temperature rising stepwise from 230° to 350° C. and then to a second calcination for 2½ hours at 400° C. The calcined catalytic material is milled to a particle size of less than 80 μm. The maximum degree of saturation of the powder is 25%.

80 l (112 kg) of rough-surfaced non-porous magnesium silicate balls commercially available as a catalyst carrier (Rosenthal Fl/Sp), having a diameter of 6 mm, are pre-moistened with 1.1 kg of water in a coating kettle of 200 liters capacity and then sprayed continuously in the kettle, through a nozzle, with 4.1 kg of water at a rate of 1.281 g of $H_2O$/min per liter of carrier, with the kettle rotating at 8 rpm. At the same time 24 kg of the catalyst powder are continuously introduced into the kettle at a rate of 7.5 g of powder per liter of carrier per minute via a belt weigher and vibrating chute, outside the spray cone of the water spray nozzle. The water content in the coating layer which develops averages 87% of the maximum degree of saturation. During coating, the powder fed in is taken up completely and no agglomeration of the catalyst particles is observed. After completion of coating, the catalyst is dried to a residual water content of 0.5% by weight with air at 110° C.

Abrasion Test 1.16 liters of catalyst are introduced at constant speed, over 30 seconds, from a belt weigher into a test pipe of 25 mm internal diameter and 3 m length; the material is then blown out of the pipe again and the amount abraded is determined. It is less than 0.01%.

(b) Gas phase oxidation of acrolein-containing reaction gases from the oxidation of propylene 1 liter of the coated catalyst is introduced into a reaction tube having an internal diameter of 25 mm, and the tube is heated to 278° C. in a salt bath. 2,217 liters (S.T.P.) per hour of a gas mixture which contains 4 percent by volume of acrolein, 0.1 percent by volume of acrylic acid, 5.15 percent by volume of water vapor, 5.6 percent by volume of oxygen, 85 percent by volume of nitrogen and 0.15 percent by volume of by-products of the oxidation of propylene, namely acetic acid, formaldehyde, maleic acid, CO and $CO_2$, are then passed over the catalyst. The acrolein conversion is 98 mole % and the yield of acrylic acid is 95 mole %.

EXAMPLE 2

(a) Preparation of the catalyst

A catalytic material having the composition 1 $V_2O_5$:0.0.26$K_2O$ is prepared by mixing potassium carbonate and vanadium pentoxide as powders, heating the mixture to 670° C. and then allowing the liquid melt to solidify in a sheet-metal trough. The solidified mass is then crushed and milled to a powder of particle size less than 50 μm. The maximum degree of saturation of the powder is 21.2%.

120 g of powder are applied at the rate of 20 g of powder/min to 1,000 g of α-Al₂O₃ balls (water absorption 1%) of 8 mm diameter which, after pre-moistening with 6 g of H₂O, are sprayed continuously, but spatially separate from the addition of the powder, with 18 g of water at a spraying rate of 3 g/min. The 30 cm rotating dish used revolves at 35 rpm. The water content of the coating which forms on the balls averages 94% of the maximum degree of saturation. The coated catalyst obtained has an extremely high abrasion resistance after having been dried, at 100° C., to a residual moisture content of 0.2%. Using the drop test described in Example 1, the abrasion is less than 0.01% by weight.

(b) Use of the catalyst for oxidizing p-t-butyltoluene to p-t-butyl-benzaldehyde and p-t-butylbenzoic acid A mixture of 2 liters (S.T.P.)/hour of p-tert.-butyltoluene, 20 liters (S.T.P.)/hour of air and 15 liters (S.T.P.)/hour of water vapor, at 412° C., is passed over a 20 cm³ sample of the catalyst in a tubular laboratory reactor having an internal diameter of 25 mm. A conversion of 22 mole % and a yield of p-t-butyl-benzaldehyde of 6.9 mole % and of p-t-butylbenzoic acid of 7.1 mole % is achieved. The combined selectivity for the two products is accordingly 68 mole %.

EXAMPLE 3

(a) Preparation of the catalyst

A catalytic material having the composition $Mo_{12}Bi_1Fe_3Ni_1Co_7B_2Sb_{0.1}K_{0.14}O_{56.7}$ is prepared by the method described in British Pat. No. 1,491,750, Example 1, and is calcined.

The resulting material is milled to a particle size of less than 30 μm. Its maximum degree of saturation is 33.4%. 156 g of the catalyst powder are applied, together with 62.2 g of water, to 100 g (=76 ml) of non-porous steatite balls of 3 mm diameter:

The steatite balls, pre-moistened with 1.0 g of water (i.e. 1% of their weight) are charged continuously, in a rotating dish of 30 cm diameter, with 17.3 g of catalyst powder/liter of carrier/min by means of a metering screw, and are sprayed with 6.9 g of water/liter of carrier/min through a two-material nozzle, using 12.5 liters (S.T.P.)/min of air at room temperature as the propellant gas; the dish revolves at 35 rpm and is inclined at 45°, and the catalyst powder impinges on the rolling balls outside the water spray cone. The water content of the coating which forms is about 67% of the maximum degree of saturation. The catalyst is then dried at 110° C. to a water content of 0.3%. The mean diameter of the coated catalyst particles obtained is 4.7 mm, corresponding to a mean coating thickness of 0.85 mm. The abrasion resistance of the catalyst is very good. In the drop test described in Example 1, using a 50 g sample, the abrasion is <0.01% by weight.

(b) Use of the catalyst for oxidizing isobutene to methacrolein

Per hour, a gaseous mixture of 3 liters (S.T.P.) of isobutene, 37.2 liters (S.T.P.) of air and 24 liters (S.T.P.) of water vapor is passed over 43 cm³ of the catalyst in a tubular laboratory reactor (tube diameter 15 mm), the bath temperature being 376° C. 94 mole % of isobutene are converted. The yield of methacrolein is 80 mole % and the yield of methacrylic acid 1 mole %; the combined selectivity for the two products is 87 mole %.

EXAMPLE 4

(a) Preparation of the catalyst

A catalytic material having the composition $Mo_{12}Ni_{8.5}Fe_2Bi_1P_{0.06}Na_{0.18}K_{0.06}Si_{10}O_x$ is prepared as follows:

561 g of aqueous bismuth nitrate solution (11% of bismuth, 5% of free nitric acid), 1,117 g of aqueous nickel nitrate solution (13.2% of nickel) and a solution of 239 g of iron nitrate in 1,240 g of water are mixed in the stated sequence. A solution of 625 g of ammonium heptamolybdate, 2.3 g of 75% strength phosphoric acid and 452 g of 25% strength ammonia solution in 3,320 g of water is added to the preceding solution. Finally, 354 g of 50% strength silica sol are also added and the resulting suspension is spray-dried.

500 g of the resulting material are kneaded with 62 g of water and 0.34 g of 48% strength potassium hydroxide solution over 1½ hours; the mixture is molded into 4.5 mm diameter extrudates and dried for 24 hours at 120° C.

The dried extrudates are calcined for 2 hours at 360° C. in the presence of air and then milled to a particle size of less than 300 μm. (The sodium content of the material results from natural impurities in the components).

The maximum degree of saturation is 48%. 2,600 g of the powder are applied continuously at a rate of 17.4 g/liter of carrier/min to 2,500 g (=1.78 liters) of the carrier balls, which are sprayed continuously with a total of 850 g of water at a rate of 5.69 g/liter of carrier/min. The magnesium silicate balls used as the carrier, which have a water absorption of 1% and a diameter of 1.5–2.5 mm, are pre-moistened, before coating, with 32 g of water and are rolled, during coating, in a rotating dish of 50 cm diameter revolving at 14 rpm at an angle of 45°. The mean degree of moistening is 71% of the maximum degree of saturation of the catalyst powder. After completion of coating, the catalyst is dried for 16 hours at 80° C. and then calcined for 1½ hours at 600° C. in a stream of air. The abrasion resistance of the catalyst is very good; using the drop test described in Example 1, in a pipe of 21 mm diameter, the abrasion is only 0.025%.

During coating, no agglomeration of the catalyst particles is observed, as was also the case in Examples 1 to 3.

(b) Use of the catalyst for the oxidation of propylene to acrolein 800 cm³ of the coated catalyst are introduced into a steel tube of 3.6 m length and 21 mm internal diameter and heated, by means of the salt bath surrounding the tube, to 342°–343° C. Per hour, a mixture of 80 liters (S.T.P.) of propylene, 800 liters (S.T.P.) of air and 800 liters (S.T.P.) of nitrogen is passed over the catalyst. The propylene conversion is 95.2 mole % and the yield of acrolein+acrylic acid is 89.5 mole %. The selectivity of formation of acrolein+acrylic acid is 94%.

At a bath temperature of 332° C., the conversion is 88.7 mole %, the yield of acrolein+acrylic acid is 84.6 mole % and the selectivity is 95.4 mole %.

EXAMPLE 5

350 g of the active material prepared as in Example 1 are applied as follows to a porous spherical α-Al₂O₃ carrier having a particle diameter of 4.7 mm, a porosity of 30% and a water absorption of 17% by weight:

0.92 liter (1,000 g) of carrier are premoistened with 36 g of water (21.2% of the water absorbency) in a coating drum of 30 cm diameter. 350 g of active material are then applied at a rate of 11.7 g/min/liter of carrier onto the carrier whilst simultaneously spraying the latter continuously with a total of 36 g of water and rotating the coating drum at 34 rpm. After completion of coating, the catalyst is dried at 120° C. to a water content of 0.4%.

To test the abrasion resistance, 50 g of the catalyst are tumbled in a rotating dish of 30 cm diameter for 3 minutes, with the dish rotating at 35 rpm, and the abrasion is determined. It is less than 0.05%, based on the weight of sample.

COMPARATIVE EXPERIMENT A

Example 5 is repeated, except that the carrier is pre-moistened with 72 g of water, ie. 42.3% of its maximum water absorbency, no water is sprayed onto the carrier simultaneously with the application of the powder, and the powder is added in 5 equal portions. Only 340 g of the powder remain adhering to the carrier, and in addition the material distribution is unsatisfactory. After drying, 13.5% by weight of the catalyst remain in the form of twin or triple agglomerates, or are insufficiently coated. The abrasion resistance of the catalyst is very poor; in the test described in Example 5, the amount abraded is 4.7%, based on the total weight.

COMPARATIVE EXPERIMENT B

Example 5 is repeated except that the carrier is not pre-moistened. The abrasion resistance of the catalyst obtained is substantially poorer than that of the catalyst obtained in Example 5; the abrasion is more than 3%.

EXAMPLES 6 TO 10

Following the procedure of Example 1, further coated catalysts are prepared with active materials having the following conventional compositions: (6) $Mo_{12}W_{1.2}V_3Cu_{2.2}Fe_{0.2}O_x$; (7) $Me_{12}W_{1.2}V_3Cu_{2.0}Mn_{0.4}O_x$; (8) $Mo_{12}W_{2.4}V_{4.6}Cu_{2.2}Cr_{0.6}O$; (9) $Mo_{12}W_{1.2}V_3Cu_2Sn_{0.5}O_x$; (10) $Mo_{12}W_{1.2}V_3Cu_{2.2}Nb_{0.2}Cr_{0.6}O_x$, the components actually added being iron(III) acetate, hydrated manganese acetate, chromium nitrate, tin(II) oxide and niobium oxide. In the abrasion test (c.f. Example 1), the abrasion is in each case less than 0.02% by weight. The catalysts are very suitable for the gas phase oxidation of acrolein to acrylic acid under otherwise conventional conditions.

EXAMPLE 11

A pulverulent mixture of 24.06 g of $V_2O_5$ and 0.44 g of $H_6TeO_6$ is fused at 670° C., as described in Example 1 of German Published Application DAS No. 2,122,664. After the material has cooled, it is crushed and milled to a powder of particle size 50μ.

The catalytic material thus prepared is applied, by the method of Example 2, to 340 g of mullite balls of diameter 5–7 mm whilst continuously moistening the balls with a total of 4.5 g of water.

The coated balls are dried to 0.4% residual moisture content.

The abrasion of the finished catalyst, determined by the method described in Example 1, is less than 0.08% by weight, based on active material.

The catalyst is, for example, very suitable for use for the gas phase oxidation of 1-methyl-3-phenylindan to anthraquinone at about 430° C.

We claim:
1. In a process for the preparation of a coated catalyst comprising
   (a) an inert carrier having a particle diameter of not less than 100 μm and a surface area of up to 20 m²/g and
   (b) a coating which firmly adheres to the outer surface and in the edge zone, near the surface, of the carrier particles, and which contains the catalytic material, by applying the catalytic material, in the form of a powder of particle size not more than 300 μm, in the presence of water, to the vigorously agitated carrier, the improvement wherein catalytically active material in an amount of from 1 to 40 g/minute/liter of carrier, and water in a weight ratio of catalytic material to water of from 1:1 to 30:1, are applied continuously and spatially separate from one another, each at a constant speed, onto the carrier particles, which may or may not have been pre-moistened with water in the amount of up to 95% of the particle absorbency, in such a way that the water content of the coating which forms is less than the maximum degree of saturation of the coating of catalytic material.

2. A process as claimed in claim 1, wherein the carrier particles have a porosity of less than 5% and are pre-moistened with from 0.1 to 2% of water, based on the weight of carrier particles 3. A process as claimed in claim 1, wherein the carrier particles have a porosity of greater than 5% and are pre-moistened with an amount of water corresponding to from 5 to 30% of their water absorbency.

4. A process as claimed in claim 1, wherein the particle size of the catalytic material is less than 50 μm.

5. A process as claimed in claim 1, wherein the coated catalyst is dried to a water content of less than 2% by weight.

6. A process for the preparation of a coated catalyst as claimed in claim 1, wherein the catalytic material has the composition $$Mo_{12}V_aW_bMe_c^1Me_d^2Me_e^3O_x$$

where
Me¹ is Cu and/or Fe, with or without Mn, P1 Me² is one or more metals from the group consisting of Sb, Sn, Cr, Nb, Ta and Ni,
Me³ is an alkali metal and/or alkaline earth metal and a is from 0.5 to 15, b is from 0.1 to 6, c is from 0.1 to 6, d is from 0 to 6 and e is from 0 to 0.1, and
X is the number of atoms required to saturate the valencies of the other constituents.

* * * * *

UNITED STATES PATENT AND TRADEMARK OFFICE
CERTIFICATE OF CORRECTION

PATENT NO. : 4,297,247

DATED : October 27, 1981

INVENTOR(S) : Richard Krabetz, Walter Herrmann, Heinz Engelbach, Peter Palm, Karl Sommer and Heinrich Spahn It is certified that error appears in the above—identified patent and that said Letters Patent is hereby corrected as shown below:

IN THE CLAIMS

Claim 6, line 55 of column 10, "P1" should be deleted.

Signed and Sealed this

Sixth Day of April 1982

[SEAL]

Attest:

GERALD J. MOSSINGHOFF

Attesting Officer — Commissioner of Patents and Trademarks